US009033043B2

(12) United States Patent
Hinkel (10) Patent No.: US 9,033,043 B2
(45) Date of Patent: May 19, 2015

(54) WETTABILITY ANALYSIS OF DISAGGREGATED MATERIAL

(75) Inventor: Jerald J. Hinkel, Houston, TX (US)

(73) Assignee: Schlumberger Technology Corporation, Cambridge, MA (US)

( * ) Notice: Subject to any disclaimer, the term of this patent is extended or adjusted under 35 U.S.C. 154(b) by 479 days.

(21) Appl. No.: 12/974,116

(22) Filed: Dec. 21, 2010

(65) Prior Publication Data

US 2012/0152547 A1 Jun. 21, 2012

(51) Int. Cl.
| | | |
|---|---|---|
| *E21B 43/16* | (2006.01) | |
| *E21B 49/00* | (2006.01) | |
| *G01N 33/24* | (2006.01) | |
| *G01N 24/08* | (2006.01) | |
| *E21B 49/08* | (2006.01) | |
| *G01N 13/00* | (2006.01) | |
| *G01N 5/00* | (2006.01) | |
| *G01N 1/28* | (2006.01) | |

(52) U.S. Cl.
CPC .............. *G01N 33/24* (2013.01); *G01N 24/081* (2013.01); *E21B 49/081* (2013.01); *E21B 43/16* (2013.01); *G01N 5/00* (2013.01); *G01N 13/00* (2013.01); *G01N 2001/2866* (2013.01)

(58) Field of Classification Search
CPC ...... G01N 24/081; G01N 13/00; E21B 43/16; E21B 43/38; E21B 47/10; E21B 49/00; E21B 49/008; E21B 49/081; E21B 43/00
See application file for complete search history.

(56) References Cited

U.S. PATENT DOCUMENTS

| | | | |
|---|---|---|---|
| 5,563,338 A | 10/1996 | Leturmy et al. | |
| 6,370,947 B1 | 4/2002 | Casati et al. | |
| 2004/0255650 A1 | 12/2004 | Moudgil et al. | |
| 2008/0159260 A1 | 7/2008 | Vobbilisetty et al. | |
| 2008/0236845 A1* | 10/2008 | Morrow et al. | 166/400 |
| 2009/0159260 A1* | 6/2009 | Ikeda et al. | 166/53 |
| 2010/0296128 A1 | 11/2010 | Young et al. | |
| 2011/0108271 A1 | 5/2011 | Hinkel et al. | |
| 2012/0085536 A1 | 4/2012 | Alboudwarej et al. | |
| 2012/0152547 A1 | 6/2012 | Hinkel | |
| 2012/0152548 A1 | 6/2012 | Hinkel et al. | |

OTHER PUBLICATIONS

International Search Report and Written Opinion of PCT Application No. PCT/US2011/065769 dated Jun. 19, 2012: pp. 1-8.
Amott, E., "Observations Relating to the Wettability of Porous Rock", SPE 1167-G, 1959, vol. 216, pp. 156-162.
Babadagli, T. et al, "Analysis of Counter-Current Gas-Water Capillary Imbibition Transfer at Different Temperatures", Journal of Petroleum Science and Engineering, 55 , 2007, pp. 277-293.
Behbahani, H. S. et al, "Simulation of Counter-Current Imbibition in Water-Wet Fractured Reservoirs", Journal of Petroleum Science and Engineering, 50, 2006, pp. 21-39.
Bennion, D. B. et al, "Formation Damage Processes Reducing Productivity of Low Permeability Gas Reservoirs", SPE 60325, 2000 SPE Rocky Mountain Regional/Low Permeability Reservoirs Symposium and Exhibition, Denver, CO, Mar. 12-15, 2000, pp. 1-19.
Bennion, D. B. et al, "Low Permeability Gas Reservoirs: Problems, Opportunities and Solutions for Drilling, Completion, Stimulation and Production", SPE 35577, Gas Technology Conference, Calgary, Alberta, Canada, Apr. 28-May 1, 1996., pp. 117-131.
Carman, P.C., "Fluid Flow Through a Granular Bed", Trans. Inst. Chem. Eng., London, 15, 1937, pp. 150-156.
Carman, P.C., "The Determination of the Specific Surface of Powders", J. Soc. Chem. Ind., 57, 1938, pp. 225-234.
Dang-Vu, T. et al, "Wettability Determination of Solids Isolated from Oil Sands", Colloids and Surfaces A: Physicochemical and Engineering Aspects, 337, 2009, pp. 80-90.
Fischer, H. et al, "Modeling the Effect of Viscosity Ratio on Spontaneous Imbibition", SPE 102641, 2006 SPE Annual Technical Conference & Exhibition held in San Antonio, TX, Sep. 24-27, 2006, pp. 1-20.
Fox, W. H. et al, "The Spreading of Liquids on Low-Energy Surfaces. II. Modified Tetrafluoroethylene Polymers", J. Colloid Science, 7, 1952, pp. 109-121.
Fuerstenau, D. W. et al, "Assessing Oxidation and the Wettability of Coal by a Film Flotation Technique", ACS Division of Fuel Chemistry Preprints, 32(1), 1987, pp. 417-424.
Gupta, A. et al, "An Improved Model for Laboratory Measurement of Matrix to Fracture Transfer Function Parameters in Immiscible Displacement", SPE 28929 1994, pp. 383-396.
Hiraski, G. et al, "Surface Chemistry of Oil Recovery from Fractured, Oil-Wet, Carbonate Formation", SPE 80988, SPE International Sumposium on Oilfield Chemistry held in Houston, TX, USA, Feb. 5-8, 2003, pp. 1-12.
Katsube, T. J., "Shale Permeability and Pore-Structure Evolution Characteristics", Geological Survey of Canada, Current Research 2000-E15, 2000, 11 pages.
Kozeny, J., Uber kapillare Leitung des Wassers im Boden, "On the capillary conduction of water through soil (ascent, infiltration and application to irrigation)", Holder-Pichler-Tempsky, A. G., Commission Publishers for the Academy of Sciences, Vienna, 1927, vol. 136, Sections 1 to 10, 37 pages.

(Continued)

*Primary Examiner* — Zakiya W Bates
(74) *Attorney, Agent, or Firm* — Rachel E. Greene; Tim Curington (57) ABSTRACT

A method for determining wettability of a solid, such as a reservoir rock material includes disaggregating the material, for example by grinding and placing the disaggregated material on the surface of the fluid. The wettability is analyzed based on whether a portion of the material floats on or sinks into the fluid. The method is well suited for heterogeneous solid materials that have mixed wetting characteristics and/or have varying surface types. The fluid can be evaluated as a potential treatment fluid or a component thereof that can be used for treating the rock formation. For example, the potential treatment fluid can include a surfactant or an oxidizing agent. A simple observation can be made whether substantially all of the material placed on the surface of the fluid sinks into the fluid, or the portions of floating and sinking material can be weighed.

31 Claims, 5 Drawing Sheets

(56) References Cited

OTHER PUBLICATIONS

Li, K. et al, "Characterization of Spontaneous Water Imbibition into Gas-Saturated Rocks", SPE 62552, 2000 SPE/AAPG Western Regional Meeting held in Long Beach, California, Jun. 19-23, 2000, pp. 1-12.

Luffel, D.L. et al, "Matrix Permeability Measurement of Gas Productive Shales", SPE 26633, 68th Annual Technical Conference and Exhibition of the Society of Petroleum Engineers held in Houston, TX, Oct. 3-6, 1993, pp. 261-270.

Ma, S. et al, "Generalized Scaling of Spontaneous Imbibition Data for Strongly Water-Wet Systems", Petroleum Society of CIM, 1995, 19 pages.

Paktinat, J. et al, "Field Case Studies: Damage Preventions Through Leakoff Control of Fracturing Fluids in Marginal/Low-Pressure Gas Reservoirs", SPE 100417, 2006 SPE Gas Tehnology Sumposium held in Calgary, Alberta, Canada, May 15-17, 2006, pp. 1-11.

Penny, G. S. et al, "Field Study of Completion Fluids to Enhance Gas Production in the Barnett Shale", SPE 100434, 2006 SPE Gas Technology Symposium held in Calgary, Alberta, Canada, May 15-17, 2006, pp. 1-10.

Rangel-German, E. R. et al, "Water Infiltration in Fractured Systems: Experiments and Analytical Model", SPE 71618, 2001 SPE Annual Technical Conference & Exhibition held in New Orleans, LA, Sep. 30-Oct. 3, 2001, pp. 1-14.

Rickman, R. et al, "A Practical Use of Shale Petrophysics for Stimulation Design Optimization: All Shale Plays Are Not Clones of the Barnett Shale", SPE 115258, 2008 SPE Annual Technical Conference & Exhibition held in Denver, CO, Sep. 21-24, 2008, pp. 1-11.

Schettler, P.D. et al, "Contributions to Total Storage Capacity in Devonian Shales", SPE 23422, SPE Eastern Regional Meeting held in Lexington, KY, Oct. 22-25, 1991, pp. 77-88.

Schettler, P.D. et al, "Gas Storage and Transport in Devonian Shales", SPE Formation Evaluation, Sep. 1989, pp. 371-376.

Scholz, M. et al, "Development of a Revised Capillary Suction Time (CST) Test", Water Conditioning and Purification, Jan. 2006, pp. 46-52.

Wu, Y. et al, "An Experimental Study of Wetting Behavior and Surfactant EOR in Carbonates with Model Compounds", SPE 99612, presented at 2006 SPE/DOE Symposium on Improved Oil Recovery held in Tulsa, OK, Apr. 22-26, 2006, Mar. 2008 SPE Journal, pp. 26-34.

Zellis, M. et al, "Soil Water Content Determination" by Karl Fischer Titration, Soil Science Society of America Journal, Jan.-Feb. 1998, vol. 62:(1): pp. 257-262.

Handy, et al., "Determination of Effective Capillary Pressures for Porous Media from Imbibition Data," SPE 1361-G, presented at Joint SPE-AIChE Meeting on May 19-20, 1959, Kansas City, MO, USA, pp. 75-80, vol. 219.

Milner, et al., "Imaging Texture and Porosity in Mudstones and Shales: Comparison of Secondary and Ion-Milled Backscatter SEM Methods," SPE 138975, presented at the Canadian Unconventional Resources & International Petroleum Conference held in Calgary, Alberta, Canada, Oct. 19-21, 2010, 10 pages total, Society of Petroleum Engineers.

* cited by examiner

WETTABILITY ANALYSIS OF DISAGGREGATED MATERIAL

FIELD

The patent specification is generally related to hydrocarbon recovery from reservoirs. More particularly, this patent specification relates to methods to characterize unconventional reservoirs and the effect of treatments on reservoir material leading to enhanced hydrocarbon recovery from such reservoirs.

BACKGROUND

Shale reservoirs throughout the world are known to contain enormous quantities of gaseous and liquid hydrocarbons. However, some aspects of the production mechanisms operative in these reservoirs are not well understood. Until fairly recently, the wettability of gas reservoirs has not been of much concern. With the exploitation of gas reserves in coal seams and shales, the so-called unconventional reservoirs, the question of wettability takes on much greater importance.

In order to develop methods to efficiently recover gas from a shale reservoir, it is very useful to gain a good understanding of the chemical nature of the shale. A productive exploitation of the shale reservoir will likely require the introduction of a fluid into the reservoir. Therefore, how that fluid interacts with the formation material is to a great degree determined by the extent to which the fluid wets the formation. Reliable test methods have been developed to measure the wettability of a material, but the methods are often beyond the capabilities of most field laboratories. Thus, it is desirable in cases hydrocarbon recovery from unconventional reservoirs such as coal seams and shale reservoirs to have improved techniques for understanding the wettability characteristics of the reservoir material that can be carried out quickly, simply and can be made in a field setting.

SUMMARY

According to some embodiments, a method for determining a wettability characteristic of a solid material with a fluid is provided. The method includes disaggregating the solid material, for example by grinding, to form disaggregated solid material; placing the disaggregated solid material on the surface of the fluid; and determining the wettability characteristic based at least in part on whether a portion of the disaggregated solid material floats on or sinks into the fluid. According to some embodiments, the solid material is a sample of a rock formation or subterranean rock formation from which hydrocarbon recovery is desired. The method is well suited to heterogeneous solid materials that have mixed wetting characteristics and/or have varying surface types.

The fluid can be evaluated as a potential treatment fluid or a component thereof that can be used for treating the rock formation. For example, the potential treatment fluid can include a surfactant or an oxidizing agent.

According to some embodiments, an observation is made whether substantially all of the disaggregated solid material placed on the surface of the fluid sinks into the fluid. Additionally, the portions of the disaggregated solid material that float on and sink into the fluid can be weighed.

According to some embodiments, the disaggregating includes grinding and sieving the material through mesh having a size of between about U.S. Standard mesh size 140 and U.S. Standard mesh size 200.

According to some embodiments, a formation treating fluid for the solid material selected is based in part on the described method. According to some embodiments, a method of enhancing hydrocarbon recovery from a subterranean formation penetrated by a wellbore is provided that includes, providing the selected treatment fluid; and pumping the fluid through the wellbore and into the subterranean rock formation so as to treat the formation.

According to some embodiments, a method of selecting an appropriate wellbore service fluid for treating a subterranean formation penetrated by a wellbore is provided that includes disaggregating a portion of the subterranean formation to form disaggregated sample material; placing the disaggregated sample material on a surface of each of a plurality of candidate fluids; and selecting a candidate fluid from the plurality based on whether at least a portion of the disaggregated solid material floats on or sinks into the selected candidate fluid. Associated methods and systems for treating a subterranean formation penetrated by a wellbore are provided. According to some embodiments, methods and systems for determining characteristics of a subterranean formation are a provided.

As used herein the term "shale" refers to mudstones, siltstones, limey mudstones, and/or any fine grain reservoir where the matrix permeability is in the nanodarcy to microdarcy range.

As used herein the term "gas" means a collection of primarily hydrocarbon molecules without a definite shape or volume that are in more or less random motion, have relatively low density and viscosity, will expand and contract greatly with changes in temperature or pressure, and will diffuse readily, spreading apart in order to homogeneously distribute itself throughout any container.

As used herein the term "supercritical fluid" means any primarily hydrocarbon substance at a temperature and pressure above its thermodynamic critical point, that can diffuse through solids like a gas and dissolve materials like a liquid, and has no surface tension, as there is no liquid/gas phase boundary.

As used herein the term "oil" means any naturally occurring, flammable or combustible liquid found in rock formations, typically consisting of mixture of hydrocarbons of various molecular weights plus other organic compounds such as is defined as any hydrocarbon, including for example petroleum, gas, kerogen, paraffins, asphaltenes, and condensate.

As used herein the term "condensate" means a low-density mixture of primarily hydrocarbon liquids that are present as gaseous components in raw natural gas and condense out of the raw gas when the temperature is reduced to below the hydrocarbon dew point temperature of the raw gas.

BRIEF DESCRIPTION OF THE FIGURES

The present disclosure is further described in the detailed description which follows, in reference to the noted plurality of drawings by way of non-limiting examples of exemplary embodiments, in which like reference numerals represent similar parts throughout the several views of the drawings, and wherein.

DETAILED DESCRIPTION

The following description provides exemplary embodiments only, and is not intended to limit the scope, applicability, or configuration of the disclosure. Rather, the following description of the exemplary embodiments will provide those skilled in the art with an enabling description for implementing one or more exemplary embodiments. It being understood that various changes may be made in the function and arrangement of elements without departing from the spirit and scope of the invention as set forth in the appended claims.

Specific details are given in the following description to provide a thorough understanding of the embodiments. However, it will be understood by one of ordinary skill in the art that the embodiments may be practiced without these specific details. For example, systems, processes, and other elements in the invention may be shown as components in block diagram form in order not to obscure the embodiments in unnecessary detail. In other instances, well-known processes, structures, and techniques may be shown without unnecessary detail in order to avoid obscuring the embodiments. Further, like reference numbers and designations in the various drawings indicate like elements.

Also, it is noted that individual embodiments may be described as a process which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be re-arranged. A process may be terminated when its operations are completed, but could have additional steps not discussed or included in a figure. Furthermore, not all operations in any particularly described process may occur in all embodiments. A process may correspond to a method, a function, a procedure, a subroutine, a subprogram, etc. When a process corresponds to a function, its termination corresponds to a return of the function to the calling function or the main function.

Furthermore, embodiments of the invention may be implemented, at least in part, either manually or automatically. Manual or automatic implementations may be executed, or at least assisted, through the use of machines, hardware, software, firmware, middleware, microcode, hardware description languages, or any combination thereof. When implemented in software, firmware, middleware or microcode, the program code or code segments to perform the necessary tasks may be stored in a machine readable medium. A processor(s) may perform the necessary tasks.

According to some embodiments, a simple method to measure the extent to which a particular fluid will wet reservoir material is provided. The techniques described allow for good estimates of the wettability of reservoir material to be made. The techniques are straight-forward, inexpensive, and require only small samples from the reservoir, rather than whole cores. Further, the techniques specifically and quantitatively address mixed-wet systems. Finally, the techniques may be used to evaluate the effect of various treatments on formation surfaces of various types, and selective treatment may result.

Figure 1:
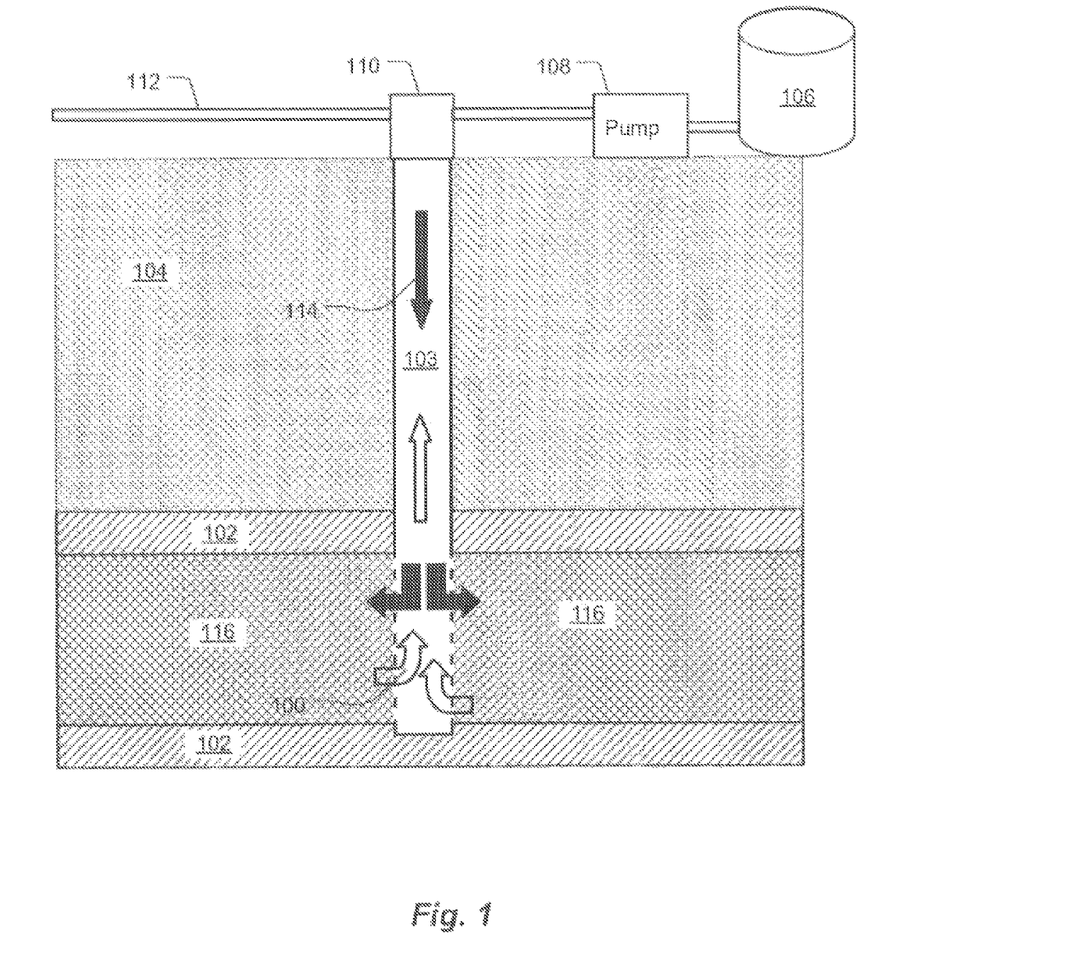
FIG. 1 illustrates a system for enhancing recovery of hydrocarbons from a low-permeability hydrocarbon reservoir, according to some embodiments.

FIG. 1 illustrates a system for enhancing recovery of hydrocarbons (in this example gas 100) from a low permeability hydrocarbon reservoir 102, according to some embodiments. The system utilizes a borehole 103 which is formed by drilling through various layers of rock (collectively, overburden 104), if any, to the low permeability reservoir 102. The reservoir 102 is described as a shale reservoir. However, according to some embodiments other types of reservoirs can benefit. For example, according to some embodiments the reservoir 102 is another type of reservoir having low permeability. It is believed that many of the techniques described herein can practically be applied to any reservoirs having low matrix permeability (i.e. between 100 nanodarcies (nD) and 500 mD, where $1\ D=9.87\times10^{-13}\ m^2$). According to some embodiments, the reservoir 102 is heterogeneous and/or has mixed wet characteristics.

The recovery enhancing system of FIG. 1 includes a fluid storage tank 106, a pump 108, a well head 110, and a gas recovery flowline 112. The fluid tank 106 contains a treating fluid formulated to promote imbibition in the low permeability reservoir 102. For example, the treating fluid may be an aqueous solution including surfactants that result in a surface tension adjusted to optimize imbibition based at least in part on determination or indication of the wettability of the shale, permeability of the shale, or both. The treating fluid 114 is transferred from the tank to the borehole using the pump 108, where the treating fluid comes into contact with the reservoir. The physical characteristics of the treating fluid facilitate migration of the treating fluid into the shale reservoir. In particular, the treating fluid enters the pore space when exposed to the reservoir, e.g., for hours, days, weeks, or longer. Entrance of the treating fluid into the pore space tends to displace gas from the pore space. The displaced gas migrates from a portion of the reservoir 116 to the borehole 103 through the pore space, via the network of natural and/or induced fractures. Within the borehole, the gas moves toward the surface as a result of differential pressure (lower at the surface and higher at the reservoir) and by having a lower density than the treating fluid. The gas is then recovered via the pipe (flowline) at the wellhead. The recovered gas is then transferred directly off site, e.g., via flowline 112.

Generally in hydrocarbon recovery from subterranean formations, sample material from a reservoir formation is scarce. Therefore, analysis techniques that make use of only small samples is advantageous. According to some embodiments, sample sizes on the order of 5g have been found to be sufficient. According to some embodiments, a measurement is made using disaggregated material, and it is understood that grinding of the sample exposes sufficient fresh surface area so as to ensuring that the test fluid is exposed to a surface very representative of that found in the undisturbed reservoir.

The use of disaggregated material is not new and the method is known to be used to evaluate the properties of extremely low permeability materials. For example, see: Schettler, P. D., Parmely, C. R., Lee, W. J., "Gas Storage and Transport in Devonian Shales" SPE Formation Evaluation, September 1989; Schettler, P. D., Parmely, C. R., "Contributions to Total Storage Capacity in Devonian Shales", SPE 23422 (1991); and Luffel, D. L., Hopkins, C. W., Schettler, P. D., "Matrix Permeability of Gas Productive Shales", SPE 26633 (1993).

Properties that can be measured using disaggregated material include permeability, porosity, and adsorption characteristics. As an example, disaggregation provides a way to determine the matrix permeability of highly fractured samples. Shales often exhibit natural fractures—even on the scale of laboratory samples. It has been found that the use of disaggregated materials provides a logical means to isolate the matrix permeability.

It is believed that the grinding of the core has only minor impact on the surface properties of the material. While the process of grinding alters the reservoir material physically, the fresh surfaces that result from grinding are believed to be quite representative of the chemical nature of the formation in its natural state. Furthermore, the surfaces of samples shaped by drilling or sawing using either oil or water lubricants do not accurately reflect in-situ properties.

Figure 2:
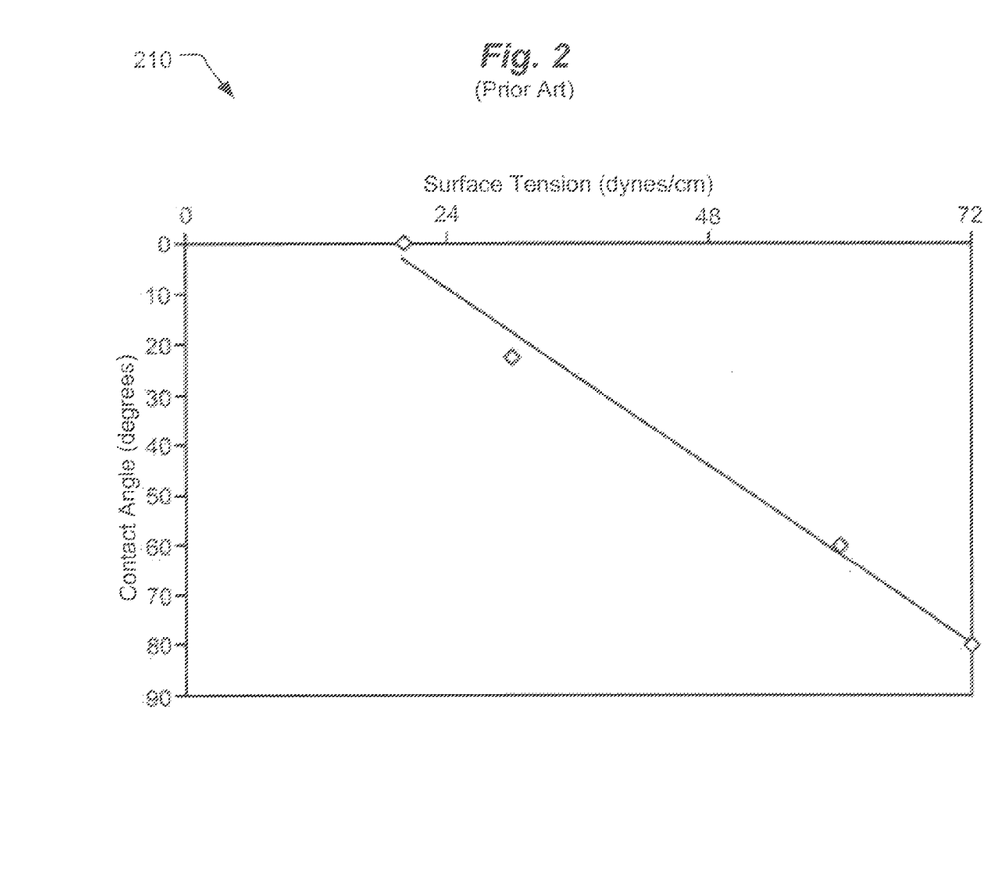
FIG. 2 shows a typical example of a conventional Zisman plot.

The wettability of a porous medium is of great interest. While reliable test methods have been developed to measure the wettability of a material, the methods are often beyond the capabilities of most field laboratories. According to some embodiments a technique is described that is based on the Zisman plot. A conventional Zisman plot is often prepared by plotting the contact angle formed by a test fluid on the surface of a medium versus the surface tension of the test fluid. FIG. 2 shows a typical example of a conventional Zisman plot. For further information on Zisman plots, see: Fuerstenau, D. W.; Williams, K. S.; Narayanan, K. S., and Diao, J. L.; "Assessing Oxidation and the Wettability of Coal by a Film Flotation Technique", ACS Division of Fuel Chemistry Preprints, 32(1) pp 417-424 (1987) (hereinafter "Fuerstenau et al."), which is incorporated herein by reference.

The Zisman plot 210 of FIG. 2 shows that the medium is not strongly water-wetting, but can be wetted by water with the addition of a surfactant. For instance, the contact angle is 80° when the test fluid (water) contains no surfactant, but the contact angle is 0° when the surface tension of the test fluid is lowered to 20 dynes/cm.

According to conventional practice, the contact angle is measured using a prepared surface and a goniometer. However, this conventional approach is unsuitable for studying typical reservoir specimens given the strong likelihood of contamination and/or alteration during preparation of the sample surface. Furthermore, in the case where a reservoir sample is quite heterogeneous, which is often the case, the results obtained will vary depending on where the drop of test fluid is placed. Accordingly, the use of a conventional goniometer method is best suited for homogeneous, non-porous substrates.

Figure 3:
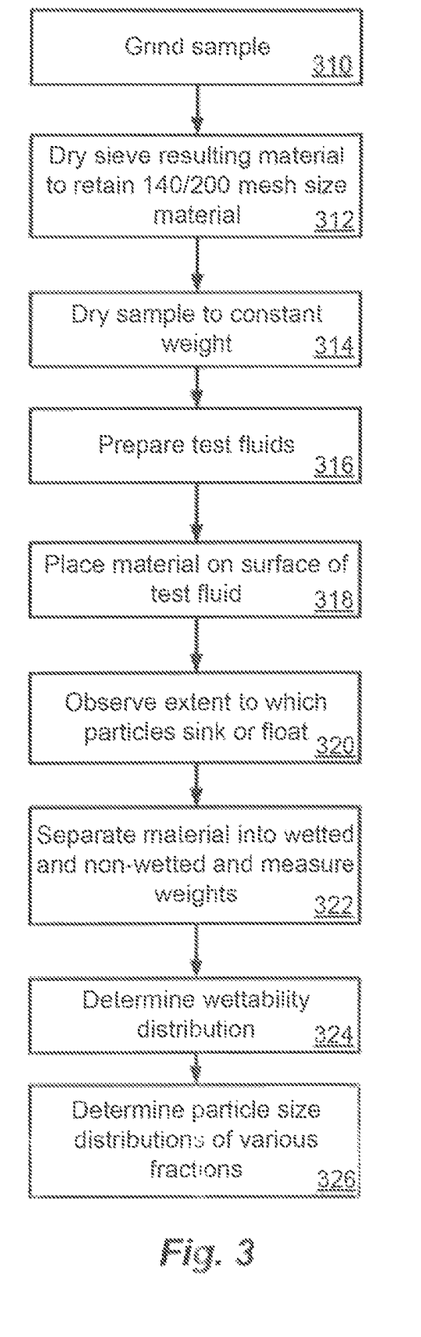
FIG. 3 is flow chart showing steps involved performing a floatation test on disaggregated material to determine wettability characteristics, according to some embodiments.

FIG. 3 is a flow chart showing steps involved in performing a floatation test on disaggregated material to determine wettability characteristics, according to some embodiments. According to some embodiments, in step 310 a formation sample is ground, for example using a SPEXSamplePrep 8000D mixer/mill. In step 312, the resulting material is dry sieved with 4 inch diameter Stainless Steel Retsch sieves on a Retsch AS200 sieve shaker and the 140/200 mesh size material fraction is retained. It has been found that this mesh size gives a fine powder that is well defined, has a narrow range of particle sizes. According to some embodiments, it has been found that a mesh size of between about U.S. Standard mesh size 140 and U.S. Standard mesh size 200 is suitable for many applications. According to some other embodiments, the suitable mesh size can be determined though a separate test. A floatation test, such shown in FIG. 3 is carried out for several different decreasing particle size ranges. When the wettability characteristics tend to stabilize, this indicates that the heterogeneity size has been approximately reached, and this is the size range that is suitable.

In Step 314, the sample is then dried to constant weight at a temperature not to exceed the static reservoir temperature in order to avoid alteration due to thermal effects.

In step 316, the test fluids are prepared by addition of methanol, another miscible low-surface tension solvent, or surfactants at varying concentrations to de-ionized water, brine or other suitable base fluid; as such, the surface tensions of the test fluids will vary. In step 318, small, pre-weighed quantities of the disaggregated reservoir material are placed onto the surface of the test fluid. In step 320, the degree of wetting is easily determined by simple observation of the extent to which particles either sink or remain floating on the surface of the test fluid. In step 322, a more sophisticated approach is carried out, according to some embodiments, wherein the material added to the test solution is separated into wetted (particles that sink) and non-wetted (particles that float) fractions and then weighed so as to allow in step 324 for a quantitative assessment of wettability distribution. For further information on useful test procedures, see: Fuerstenau et al.; and Dang-Vu, T.; Jha, R.; Wu, S.; Tannant, D. D.; Masliyah, J.; and Xu, Z,; "Wettability Determination of Solids Isolated from Oil Sands", Colloids and Suraces A: Physicochem. Eng. Aspects 337 (2009) 80-90, which is incorporated herein by reference. Note that it may be necessary to observe the tests for some time, as wetting may occur gradually. The following discusses a typical result for a mixed-wet sample.

Figure 4:
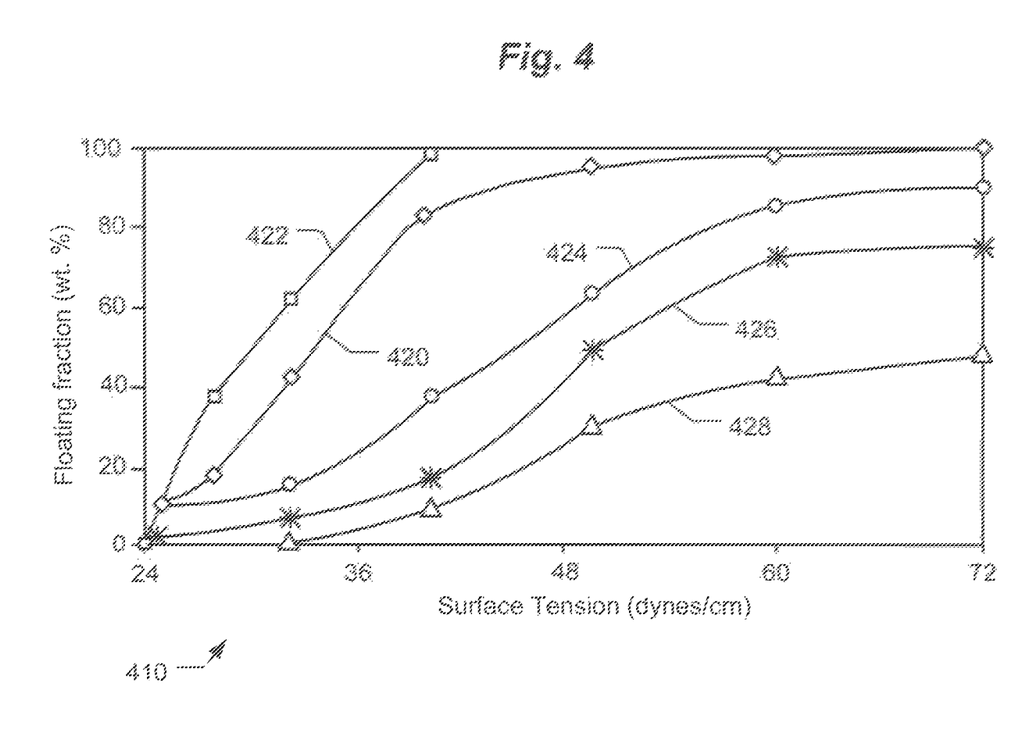
FIG. 4 is a plot showing results of a floatation test conducted using a disaggregated sample, according to some embodiments.

As shown in plot 410 of FIG. 4, various fractions of the disaggregated material are wetted as the surface tension of the test fluid is varied. Therefore the described method, according to some embodiments, is particularly well suited to the study of heterogeneous, also known as mixed-wet, materials. The test of FIG. 3, according to some embodiments, is repeated for multiple fluids having different surface tensions such that a direct measure of the distribution of materials according to surface energy such as shown in curve 420, as opposed to a conventional goniometer test show in the plot of FIG. 2, which provides a global average. According to some embodiments, repeating the test of FIG. 3, and building multiple profile curves such as shown in FIG. 4, is used in selecting suitable treatment fluids for treating subterranean formations.

The circles (curve 424), the asterisks (curve 426) and the triangles (curve 428) represent increasing hydrophilicity as evidenced by the lower percentage of floaters in each successive curve. Increased hydrophobicity is indicated by the squares (curve 422).

According to some embodiments, different additives that alter wetting characteristics are tested in order to evaluate the impact of a treatment on the formation. In this example, the plot of curve 420 (diamonds) represents an as-received, unaltered formation sample and the other curves 422, 424, 426 and 428, represent differential wetting alteration through the use of certain additives. In this way the impact of a treatment can be discerned.

According to some embodiments the curve in plot 410 are used to evaluate oil wetting induced by different surfactants. In this example, curve 428 (triangles) represents a virgin water-wet rock. The other curves 422, 420, 424 and 426 represent the extent of oil-wetting induced by different surfactants. According to an alternate embodiment, curve 422 (squares) represents data that were obtained from an as-received, properly selected sample, this result would be representative of a significantly oil-wet formation.

According to some embodiments, an additional step 326, in FIG. 3, is provided where the particle size distributions of the various fractions are determined. The particle size distribution information allows for an estimate of total surface area. The surface area and surface energy data may be used to estimate contact angles representative of the various fractions.

As previously mentioned, the surface chemistry of the naturally occurring shale samples is variable and complex, both in its chemical composition, and in its texture. A given sample may contain microscopic regions that have a distribution of different surface energies, and as such widely different wetting characteristics. It has been found in U.S. patent application Ser. No. 12/914,463 (hereinafter "the '463 patent application") that the initiation of imbibition is often not a linear function as predicted by the model described in that application. It is possible that the observed induction period of the experiment is the result of a distribution of mixed wetting regions on the surfaces of the particles in the pack, and/or the result of pore size distribution in the material. According to some embodiments, an floatation test analysis method as shown in FIG. 3 can be used to determine how variable the distributions of surface energies are for a given rock, and how prone they are to alteration.

Figure 5:
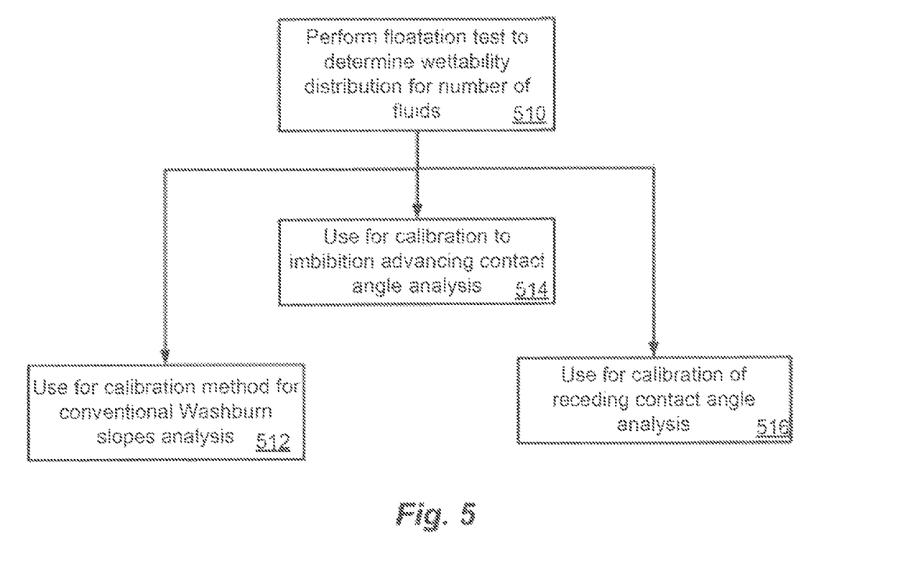
FIG. 5 is a flow chart showing steps for combining the technique of FIG. 3 with other experimental configurations, according to some embodiments.

According to some other embodiments, the floatation test analysis of FIG. 3 is amenable to other experimental configurations. By using a series of wetting phase fluids with a range of surface tensions (such as a controlled series of water methanol solutions) more knowledge about the surface energy distributions in complex shale samples can be gained. FIG. 5 is a flow chart showing steps for combining the technique of FIG. 3 with other experimental configurations, according to some embodiments. In step 510, the floatation test as shown in FIG. 3 is carried out for a number of fluids. In step 512 the results of the floatation tests are used in combination with a conventional slopes analysis which is described more fully in the '463 patent application. In a conventional Washburn slopes analysis, it has been customary to determine the contact angle of an unknown fluid by comparing its performance in an imbibition test with that of a baseline fluid, or calibration fluid, whose contact angle is believed to be known. Often, the assumption is made that the baseline fluid wets the porous solid perfectly; this is equivalent to assuming that the fluid forms a contact angle of 0 degrees. Using the results of the floatation test, a suitable fluid can be selected as this baseline fluid.

In the '463 patent application, a modified Washburn imbibition measurement of the advancing contact angle is also described. According to some embodiments, in step 514, the floatation test results from step 510 are combined with the modified Washburn approach described in the '463 patent application. In particular, technique is very useful for characterizing formation material that have contact angles of 90° or greater when exposed to pure water, since in such cases a conventional imbibition test cannot be carried out.

As can be seen in FIG. 2, that lowering the surface tension of the fluid to a value less than 24 dynes/cm provides near perfect wetting. Such a fluid should provide an advancing contact angle of very nearly 0°. According to some embodiments, this result can be compared to the value determined using our method thereby providing further opportunity to calibrate the methods described in the '463 patent application.

In step 516, the floatation test results are combined with methods described in commonly-assigned Unites States patent application Entitled "Method to Characterize Underground Formation" filed simultaneously with the present application (hereinafter "the Receding Contact Angle" patent application"), incorporated herein by reference, describes a centrifuge method to measure the drainage contact angle. According to some embodiments, this method of the "Receding Contact Angle" patent application is enhanced by using an analysis method as shown in FIG. 3. The equation:

$$\cos\theta_A = \frac{P_{pro}\sqrt{k_A}}{3.264\gamma_A\sqrt{\phi_A^3}}$$

shows how one may determine the product of the surface tension and the cosine of the receding contact angle. A series of tests can be performed where the surface tension of the test fluid is varied. Normally, the surface tension of the test fluid will remain unchanged during a test, but a sample can be readily obtained for a measurement of surface tension, thereby allowing for a determination of average contact angle as a function of surface tension.

It should be noted that although the embodiments have been described with respect to recovery of hydrocarbon from a source formation, according to some embodiments techniques described herein are also applied to a source that is obtained via mining operations, e.g., surface mining or sub-surface mining, especially in the case of coal seams (coalbed methane). For example, material obtained from surface mining could be treated with fluid to recover or remove hydrocarbon from the material.

While the invention is described through the above exemplary embodiments, it will be understood by those of ordinary skill in the art that modification to and variation of the illustrated embodiments may be made without departing from the inventive concepts herein disclosed. Moreover, while the preferred embodiments are described in connection with various illustrative structures, one skilled in the art will recognize that the system may be embodied using a variety of specific structures. Accordingly, the invention should not be viewed as limited except by the scope and spirit of the appended claims.

What is claimed is:

1. A method for determining a wettability characteristic of a solid material with a fluid comprising:
   disaggregating the solid material to form a plurality of particles of disaggregated solid material;
   placing the disaggregated solid material on a surface of the fluid; and
   determining the wettability characteristic based at least in part on whether at least a portion of the disaggregated solid material floats on or sinks into the fluid, wherein the determining includes weighing the portion of the disaggregated solid material that floats on the fluid, and weighing the portion of the disaggregated solid material that sinks into the fluid.

2. A method according to claim 1 wherein the solid material is a sample of a rock formation from which hydrocarbon recovery is desired.

3. A method according to claim 2 wherein the rock formation is a subterranean rock formation penetrated by a wellbore.

4. A formation treating fluid for the solid material selected based in part on a method according to claim 3.

5. A method of enhancing hydrocarbon recovery from a subterranean formation penetrated by a wellbore, the method comprising:
   providing a treatment fluid according to claim 4; and
   pumping the fluid through the wellbore and into the subterranean rock formation so as to treat the formation.

6. A method of evaluating effects of a treatment preformed to alter wettability of a subterranean formation material, the method comprising:
   pumping a treatment fluid through the so as to treat the formation; and evaluating effects of the treatment fluid to wettability of the subterranean formation material based in part on the method of claim 3, wherein the solid material is a sample of the formation material.

7. A method according to claim 2 further comprising evaluating the fluid as a potential treatment fluid or a component thereof that can be used for treating the rock formation based at least in part on the determined wettability characteristic.

8. A method according to claim 7 wherein the potential treatment fluid or a component thereof is a surfactant.

9. A method according to claim 7 wherein the potential treatment fluid or a component thereof is an oxidizing agent.

10. A method according to claim 7 wherein the potential treatment fluid or a component thereof is for use following a fracturing treatment.

11. A method according to claim 1 wherein the solid material is primarily heterogeneous.

12. A method according to claim 11 wherein the heterogeneous solid material has mixed wetting characteristics with respect to the fluid.

13. A method according to claim 11 wherein the heterogeneous solid material has surfaces of various types.

14. A method according to claim 1 wherein the determining includes observing whether substantially all of the disaggregated solid material placed on the surface of the fluid sinks into the fluid.

15. A method according to claim 1 wherein the wettability characteristic is used to calculate a contact angle for the fluid and the solid material.

16. A method according to claim 1 further comprising carrying out imbibition testing on the solid material; and combining one or more results of the imbibition testing with the determined wettability characteristic.

17. A method according to claim 1 further comprising carrying out a testing procedure on the solid material to determine a receding contact angle for the solid material; wherein the receding contact angle is based in part on the determined wettability characteristic.

18. A method according to claim 1 wherein the disaggregating includes a grinding of the solid material to form the disaggregated solid material.

19. A method according to claim 18 wherein the disaggregating includes sieving through mesh having a size of between about U.S. Standard mesh size 140 and U.S. Standard mesh size 200.

20. A method according to claim 1 further comprising:
repeating the placing and determining for one or more other fluids; and
generating a profile relating a function of surface tension and a function of wetted surface area.

21. A method according to claim 1 further comprising:
repeating the placing and determining for one or more other fluids; and
selecting a treatment fluid based in part on the determined wettability characteristics for the fluids.

22. A method of selecting an appropriate wellbore service fluid for treating a subterranean formation penetrated by a wellbore comprising:
disaggregating a portion of the subterranean formation to form a plurality of particles of disaggregated sample material;
placing the disaggregated sample material on a surface of each of a plurality of candidate fluids; and
selecting a candidate fluid from the plurality based at least in part on whether at least a portion of the disaggregated solid material floats on or sinks into the selected candidate fluid, the selected candidate fluid forming at least part of the wellbore service fluid, wherein the determining includes weighing the portion of the disaggregated solid material that floats on the fluid, and weighing the portion of the disaggregated solid material that sinks into the fluid.

23. A method of treating a subterranean formation penetrated by a wellbore the method comprising:
providing a wellbore service fluid selected according to claim 22; and
pumping the fluid through the wellbore and into the subterranean formation so as to treat the formation.

24. A system for enhancing hydrocarbon recovery from a subterranean formation penetrated by a wellbore comprising:
a container that stores a treating fluid, said treating fluid selected according to claim 22; and
a pumping system adapted and configured to transfer the treating fluid from the container and into the wellbore and the formation.

25. A method of determining a wettability characteristic of subterranean formation penetrated by a wellbore comprising:
disaggregating a portion of subterranean formation to form a plurality of particles of disaggregated sample material;
analyzing the disaggregated sample material; and
determining the wettability characteristic based at least in part on the analysis of the disaggregated sample material; wherein the determining includes weighing the portion of the disaggregated solid material that floats on the fluid, and weighing the portion of the disaggregated solid material that sinks into the fluid.

26. A method according to claim 25 wherein the determining includes placing the disaggregated sample material on a surface of a fluid, and the wettability characteristic being based at least in part on whether at least a portion of the disaggregated solid material floats on or sinks into the fluid.

27. A method according to claim 25 wherein the disaggregated sample material is selected based on particle sizes.

28. A method according to claim 27 wherein the disaggregation exposes fresh surface area of the material.

29. A method of determining suitable particle sizes for disaggregated material from a solid material for use in wettability analysis comprising:
disaggregating the solid material to form a plurality of particles of disaggregated solid material of a first particle size range;
determining one or more wettability characteristics of the disaggregated solid material of a first particle size range; wherein the determining includes weighing the portion of the disaggregated solid material that floats on the fluid, and weighing the portion of the disaggregated solid material that sinks into the fluid;
repeating the disaggregating and determining for one or more other particle size ranges; and
selecting a suitable particle size range based on the determined one or more wettability characteristics for the first and one or more other particle size ranges.

30. A method according to claim 29 wherein the determining of the one or more wettability characteristics includes placing the disaggregated solid material on a surface of a fluid and determining at least one of the wettability characteristics based at least in part on whether at least a portion of the disaggregated solid material floats on or sinks into the fluid.

31. A method according to claim 29 wherein the suitable particle size range is selected when the one or more determined wettability characteristics stabilizes over more than one particle size range.

* * * * *